United States Patent
Dombeck et al.

(10) Patent No.: US 11,092,979 B2
(45) Date of Patent: Aug. 17, 2021

(54) INTRODUCTION OF OLFACTORY CUES INTO A VIRTUAL REALITY SYSTEM

(71) Applicant: Northwestern University, Evanston, IL (US)

(72) Inventors: Daniel Andrew Dombeck, Evanston, IL (US); Brad Allen Radvansky, Chicago, IL (US)

(73) Assignee: Northwestern University, Evanston, IL (US)

( * ) Notice: Subject to any disclaimer, the term of this patent is extended or adjusted under 35 U.S.C. 154(b) by 56 days.

(21) Appl. No.: 16/182,793

(22) Filed: Nov. 7, 2018

(65) Prior Publication Data

US 2019/0346865 A1 Nov. 14, 2019

Related U.S. Application Data

(60) Provisional application No. 62/670,353, filed on May 11, 2018.

(51) Int. Cl.
*G05D 7/06* (2006.01)
*G05B 15/02* (2006.01)
*G06F 3/01* (2006.01)

(52) U.S. Cl.
CPC ........... *G05D 7/0617* (2013.01); *G05B 15/02* (2013.01); *G06F 3/011* (2013.01)

(58) Field of Classification Search
CPC ....... G05B 15/02; G05D 7/0617; G06F 3/011; G06F 2111/18; A61K 2800/56
See application file for complete search history.

(56) References Cited

U.S. PATENT DOCUMENTS

| | | | |
|---|---|---|---|
| 2009/0104072 A1* | 4/2009 | Ando | A61L 9/125 422/5 |
| 2016/0225188 A1* | 8/2016 | Ruddell | G06F 3/011 |
| 2018/0027882 A1* | 2/2018 | Hepworth | A61M 15/06 |
| 2018/0249702 A1* | 9/2018 | Burgeson | B65D 23/003 |
| 2019/0192965 A1* | 6/2019 | Chapman | A63F 13/50 |
| 2019/0196576 A1* | 6/2019 | Saarinen | G06T 19/006 |
| 2019/0215349 A1* | 7/2019 | Adams | A63F 13/54 |
| 2019/0262739 A1* | 8/2019 | Reichow | A61L 9/01 |

OTHER PUBLICATIONS

Andrieu et al., "Pulse Width Modulation Applied to Olfactory Stimulation for Intensity Tuning," PLOS ONE, Dec. 28, 2015, vol. 10, No. 12, pp. 1-12.

(Continued)

*Primary Examiner* — Chad G Erdman
(74) *Attorney, Agent, or Firm* — Bell & Manning LLC

(57) ABSTRACT

A virtual reality (VR) olfactory apparatus includes an odorant saturation chamber having an inlet and an outlet. At least a portion of the odorant saturation chamber includes a plurality of beads and a liquid. The liquid includes an odorant concentrate. The inlet extends into this portion of the odorant saturation chamber. The VR apparatus also includes a mass flow controller to generate an air flow to the inlet of the odorant saturation chamber such that the air flow passes through the portion of the odorant saturation chamber to form an odorant. The air flow passes the odorant through the outlet of the odorant saturation chamber. The VR apparatus further includes a nose chamber connected to the outlet and configured to receive the odorant.

19 Claims, 13 Drawing Sheets

(56) References Cited

OTHER PUBLICATIONS

Ischer et al., "How Incorporation of Scents Could Enhance Immersive Virtual Experiences," Front Psychol., Jul. 2014, vol. 5, No. Article 736, pp. 1-11.
Rajasethupathy et al., "Projections from Neocortex Mediate Top-Down Control of Memory Retrieval," Nature, Oct. 29, 2015, vol. 526, pp. 653-659.
Zybura et al., "Olfaction for Virtual Reality," Quarter Project, Industrial Engineering 543, University of Washington, Winter 1999 for Professor Tom Furness, pp. 1-10.

\* cited by examiner

INTRODUCTION OF OLFACTORY CUES INTO A VIRTUAL REALITY SYSTEM

CROSS-REFERENCE TO RELATED APPLICATION

The present application claims the priority benefit of U.S. Provisional Patent App. No. 62/670,353 filed on May 11, 2018, the entire disclosure of which is incorporated by reference herein.

GOVERNMENT LICENSE RIGHTS

This invention was made with government support under grant/award number 1R01MH101297 awarded by the National Institutes of Health (NIH). The government has certain rights in the invention.

BACKGROUND

Virtual reality refers to a computer-generated simulation of a three-dimensional (3D) image or environment that a user is able to interact with. The user can be a human or animal, depending on the system. The user is able to interact with the simulation via special electronic equipment such as a helmet or headset with a screen inside, gloves or other clothing/accessories that are fitted with sensors, actuators, etc. In addition to visual cues, a virtual reality simulation can also be enhanced with other sensory cues to improve the user experience. For example, sensors and/or actuators can be used to provide a tactile experience for the user in conjunction with the visual cues. Additionally, speakers can be incorporated into the virtual reality system to provide the user with audible cues in addition to the visual cues.

SUMMARY

An illustrative virtual reality (VR) olfactory apparatus includes an odorant saturation chamber. The odorant saturation chamber includes an inlet and an outlet. At least a portion of the odorant saturation chamber includes a plurality of beads and a liquid, where the liquid includes an odorant concentrate. The inlet extends into the portion of the odorant saturation chamber that includes the plurality of beads and the liquid. The VR apparatus also includes a mass flow controller configured to generate an air flow to the inlet of the odorant saturation chamber such that the air flow passes through the portion of the odorant saturation chamber that includes the plurality of beads and the liquid to form an odorant. The air flow passes the odorant through the outlet of the odorant saturation chamber. The VR apparatus further includes a nose chamber connected to the outlet of the odorant saturation chamber and configured to receive the odorant.

An illustrative method for providing olfactory cues in a virtual reality system includes determining, by a processor, a virtual velocity and a virtual bearing of a user in a virtual reality environment. The method also includes determining, by the processor, a future virtual location of the user within the virtual reality environment and a time at which the user is to arrive at the future virtual location based at least in part on the virtual velocity and the virtual bearing. The method further includes identifying, by the processor, an odorant associated with the future virtual location of the user in advance of the time at which the user is to arrive at the future virtual location within the virtual reality environment. The method further includes controlling, by the processor, one or more mass flow controllers to release the odorant into a nose chamber at the time at which the user is to arrive at the future virtual location.

Other principal features and advantages of the invention will become apparent to those skilled in the art upon review of the following drawings, the detailed description, and the appended claims.

BRIEF DESCRIPTION OF THE DRAWINGS

Illustrative embodiments of the invention will hereafter be described with reference to the accompanying drawings, wherein like numerals denote like elements.

DETAILED DESCRIPTION

Figure 1:
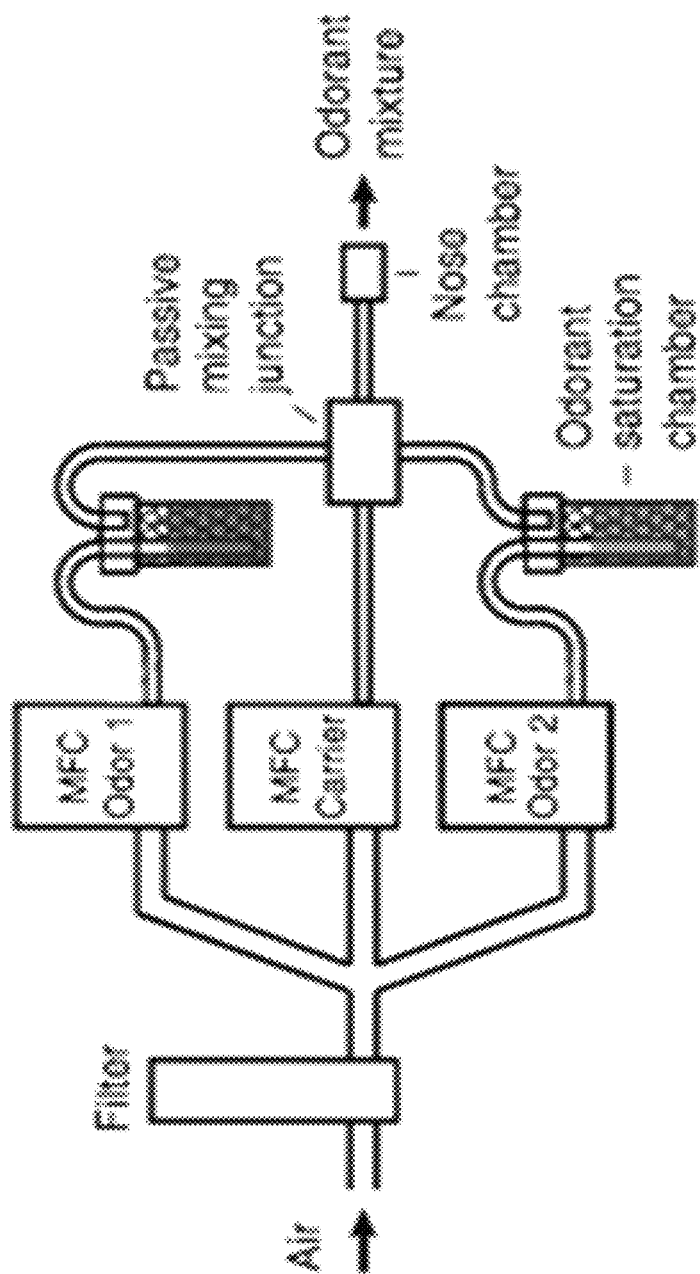
FIG. 1 depicts an odorant delivery system for virtual reality in accordance with an illustrative embodiment.

Virtual reality systems can be used for entertainment such as watching a movie, playing a video game, watching a sporting event, etc. Virtual reality systems function by immersing a user into a simulation that he/she experiences through visual cues, tactile cues, and/or audible cues. Olfactory cues (i.e., smells) can also be incorporated into a virtual reality system. However, as discussed herein, traditional olfactory systems are unable to provide a continuous olfactory experience for an adequate duration of time. Additionally, traditional olfactory systems are unable to change/update the olfactory cues rapidly enough to account for traversal of a virtual reality environment by a human or animal.

Virtual reality systems also offer unique experimental capabilities for studying the neural basis of animal behavior. This technology provides precise control over the animal's sensory environment, and therefore can be used to establish relationships between sensory features of an environment and the tuning properties of individual neurons that can be difficult to discern in real-world conditions. Virtual reality enables experiments that are either not possible or difficult to realize in real environments, such as generating cue conflict stimuli, delivering non-natural sudden changes in stimuli at particular locations, and observing sensory-driven behavior in isolation from other sensory information, such as walls/borders, textures, self-generated odors, and vestibular cues. Importantly, behaving animals can be head-restrained in VR, allowing for the application of advanced brain recording and stimulating techniques, such as whole-cell patch clamping, two-photon imaging, and two-photon stimulation that can reveal the underlying behavior of circuit, cellular, and sub-cellular mechanisms.

The vast majority of virtual reality (VR) studies to date have used visually defined environments. Tactile and auditory VR systems have also been established. However, despite the importance of odor-driven behaviors for mammals, few attempts have been made to fully incorporate odor into a VR system, either for entertainment purposes or for experimental/research purposes. In some studies, olfactory cues have been delivered to a mouse via airflow in an on/off manner during immersion in different visual or multisensory VR environments in order to create a contextual association with other stimuli. In other studies, creative use of odor trails drawn on a treadmill has been validated for studying odor tracking in rats.

However, as discussed above, a method to control odorant concentration as a continuous function of virtual space does not currently exist. Traditional virtual reality olfactometers operate with a delay of 0.5-1 s, which is too slow to provide a reproducible and high-resolution odorant spatial distribution. For example, rodents run at variable speeds on the order of ~0.5 meters/second (m/s), have sniff at rates of 3-12 Hertz (Hz), and can perform odor-driven behaviors on the order of ~100 milliseconds (ms). Humans can also move at rapid speeds within a VR environment, which limits the ability of traditional systems to provide a continuous olfactory function. Because of these limitations in traditional systems, mammalian VR experiments have been restricted to using odor as a categorical variable. While this approach has allowed for studying high-level cognitive processes, such as associational memory, it is insufficient for addressing more elementary questions of how the brain can represent and generate behaviors within a continuous olfactory world. To address such questions, described herein is an olfactory VR system capable of controlling odors as continuous spatial variables. To validate this system for behavioral and neural applications for head-fixed mice, an olfactory virtual navigation behavior was established that engages hippocampal place cells. Analysis of the resulting data demonstrates that an environment comprised of only olfactory features, combined with self-motion cues, can engage hippocampal cognitive mapping mechanisms in mammals.

To control a continuous odorant distribution across virtual space involves rapid odorant delivery/clearance relative to the timescale of the user's movement, which depends on the type of user and the type of simulation. Further, to maintain this distribution for the duration of a VR session (which can involve watching a full length movie, playing a video game, etc.) requires consistent odorant delivery with minimal depletion over time. To achieve these criteria, described herein is an odorant delivery system that includes the fastest available mass flow controllers (MFCs), the smallest tube/bottle volumes possible without compromising airflow, and a rapid odorant distribution system and technique.

FIG. 1 depicts an odorant delivery system for virtual reality in accordance with an illustrative embodiment. As depicted, the odorant delivery system (or olfactometer) includes two independent odorant streams. In alternative embodiments, fewer or additional odorant streams (and corresponding hardware) such as 1, 3, 5, 10, etc. may be used. In one embodiment, a flow rate of 0.001-0.1 Liter/minute (L/min) is passed through rapid odorant saturation chambers associated with each odorant. Mass flow controllers associated with each odorant can be used to control the flow rate. As shown in FIG. 1, a third carrier stream having a flow rate of ~0.8-1 L/min (generated by a third mass flow controller) and containing blank air is directed to a passive mixing chamber along with flows from the odorant saturation chambers. Alternatively, a different flow rate may be used for the carrier stream.

The passive mixing chamber is in fluid communication with a nose chamber that is positioned proximate to a nose of the user. This configuration allows for the concentrations of any number of different odorants to be controlled continuously and independently. To vary olfactory stimulation without varying perceived airflow, the carrier stream can be updated dynamically to maintain a constant total flow rate through the nose chamber. In one embodiment, the constant total flow rate can be 1 L/min. Alternatively, a different value may be used. The carrier stream can also be controlled independently to simulate variation in wind flow. To rapidly clear the odorants, the nose chamber can be configured to cover a nose of the user and to create a micro-environment of a known volume (e.g., 0.07 $cm^3$ for a mouse) in which the gas volume is replaced by the 1 L/min airflow every duration. In one embodiment, the duration can be 4 ms, although other values may be used in different embodiments. In one embodiment, the nose chamber is designed to not touch the nose and/or facial hair of the user.

To overcome the problems of delivery speed and consistency in an olfactometer, mouse experiments were performed using the system of FIG. 1 with two distinct odorants, methyl valerate (bubblegum smell) and α-pinene (pine smell). These odorants were used with vapor pressures high enough to continuously saturate the vapor phase, but low enough to not significantly deplete the liquid phase over time (e.g., 11.2 and 4.9 mm Hg at 25° C., respectively). In alternative embodiments, different vapor pressures may be used. The rapid odorant saturation chambers were designed in an effort to maintain steady-state saturation of the vapor phase in each odorant stream and to generate perceptible but not overpowering scents at the nose chamber. For each odorant path, the air stream was bubbled through 12 mL of odorant solution. For the methyl valerate odorant, the odorant solution was formed of a 1:125 ratio of methyl valerate to mineral oil. For the α-pinene odorant, the odorant solution was formed of a 1:37.5 ratio of α-pinene to mineral oil. In alternative embodiments, different ratios may be used. In other alternative embodiments, a liquid other than mineral oil may be used to form the odorant solutions.

Figure 2:
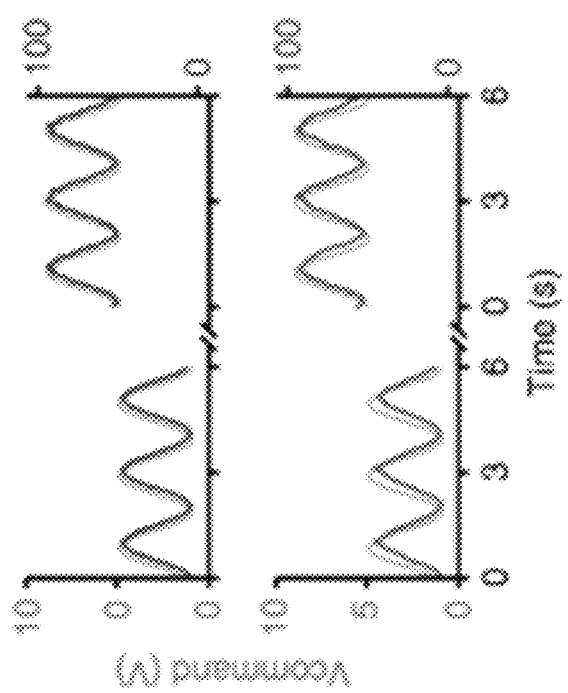
FIG. 2 depicts continuous odorant delivery following a 0.5 Hz sinusoidal command of low and high offset in accordance with an illustrative embodiment.

The odorant saturation chambers were formed as a 40 mL vial that was filled with beads, such as 3 mm glass beads. Two thirds of each odorant saturation chamber was also filed with an odorant solution. This configuration increased the interaction of air with the odorant solution first by bubbling in through the bottom two thirds of the chamber that contains the odorant solution, and then by passing through the increased solution surface area generated by the coated beads in the top third of the saturation chamber. A photo-ionization detector (PID) was used to measure the response time and depletion of the olfactometer (measured at the nose chamber). When driven by 0.5-Hz sinusoids, the olfactometer delivered odorants as continuous variables with a delay of $0.148 \pm 0.059$ s for methyl valerate and $0.183 \pm 0.070$ s for α-pinene (n=300 cycles: 150 low-offset and 150 high-offset). FIG. 2 depicts continuous odorant delivery following a 0.5 Hz sinusoidal command of low and high offset in accordance with an illustrative embodiment. These delivery rates are on the order of a sniffing cycle for a mouse.

Figure 3:
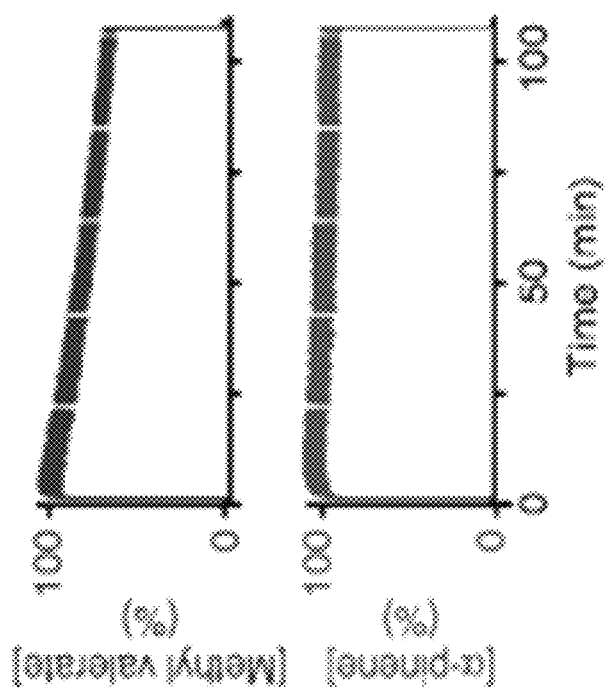
FIG. 3 depicts odorant decay based on delivery at a constant flow rate over a 100 minute period of time in accordance with an illustrative embodiment.

FIG. 3 depicts odorant decay based on delivery at a constant flow rate over a 100 minute period of time in accordance with an illustrative embodiment. In the depiction of FIG. 3, small gaps occur where baseline measurements were taken to calibrate the PID used to perform the measurements at the nose chamber. At a maximum flow rate of 0.1 L/min for ~100 min, the odorant concentrations decayed with time constants of 242 minutes and 1027 minutes for methyl valerate and α-pinene, respectively. This means that over a typical behavioral session length of 30 min, the fastest-depleting odorant, methyl valerate, would be reduced in magnitude by at most 12%. The proposed odorant delivery system therefore includes the mechanical components capable of rapid and reliable control of odorants in VR.

The olfactometer (or odorant delivery system) of FIG. 1 was incorporated into a visual VR system and driven using modified VR software to account for the incorporation of olfactory cues. This permitted the options of synchronizing or desynchronizing the visual and olfactory aspects of the VR system, and also using one or the other sensory modality alone.

Figure 4:
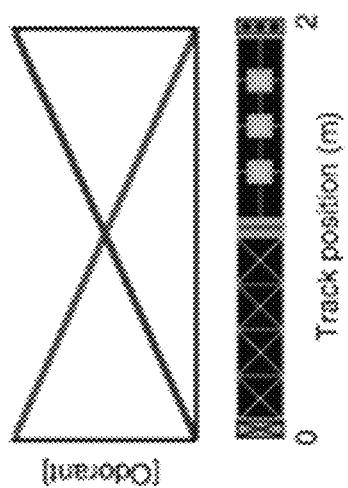
FIG. 4 depicts smooth odorant spatial distributions in accordance with an illustrative embodiment.
Figure 5:
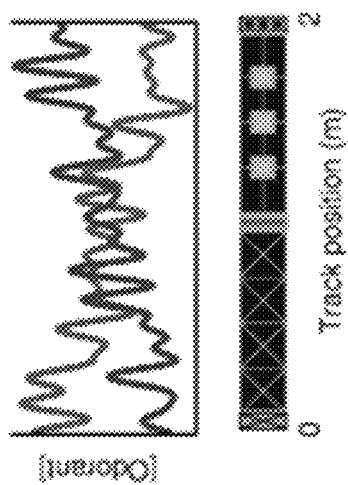
FIG. 5 depicts noisy odorant spatial distributions relative to a linear track used in a simulation in accordance with an illustrative embodiment.

As known in the art, real-world odorant distributions can occur as concentration gradients caused by molecular diffusion, as distributed bursts of high-concentration plumes caused by turbulence, or as a combination of these two resulting in concentration gradients with added noise. Accordingly, animals have been shown to use gradient-ascent and/or sparse-searching strategies under different conditions. To allow for the study of gradient-guided navigation, use of the system has demonstrated that it can generate smooth spatial distributions of methyl valerate and α-pinene across a linear track used for the simulation, as depicted in FIG. 4. Specifically, FIG. 4 depicts smooth odorant spatial distributions in accordance with an illustrative embodiment. The real-world generation of odorant plumes by air turbulence is an ongoing focus of fluid dynamics research, making it difficult to simulate precisely a true turbulent odorant distribution in virtual reality. However, testing demonstrated that the proposed system can generate a noisy odorant distribution, as well as turbulent-like plumes. FIG. 5 depicts noisy odorant spatial distributions relative to a linear track used in the simulation in accordance with an illustrative embodiment.

Two challenges that needed to be overcome for the precise control of odorant distributions were: 1) mechanical delay of odorant delivery through the olfactometer, which is discussed above, and 2) variable locomotion velocity of the user within the VR environment requiring rapid changes in odorant flow rates. Combined, these problems resulted in a skewed odorant spatial distribution in which the user received concentrations corresponding to a previous position rather than its current position. To correct for this, an algorithm was developed that delivered odorants based on a prediction of the future position of the user within the VR environment. This algorithm used the instantaneous position and velocity of the user at each update iteration (~5 ms) of VR to predict the position at one odorant mechanical delay period in the future. Instantaneous velocity was calculated by averaging the previous several $\Delta position/\Delta time$ measurements within a previously determined time window. In one embodiment, the time window was determined offline by minimizing the error between real and predicted position of the user. Implementing the position-predictive algorithm eliminated the skew in concentration and tightened the odorant spatial distributions by factors of 4.4 and 3.7 for methyl valerate and α-pinene, respectively.

Figure 6B:
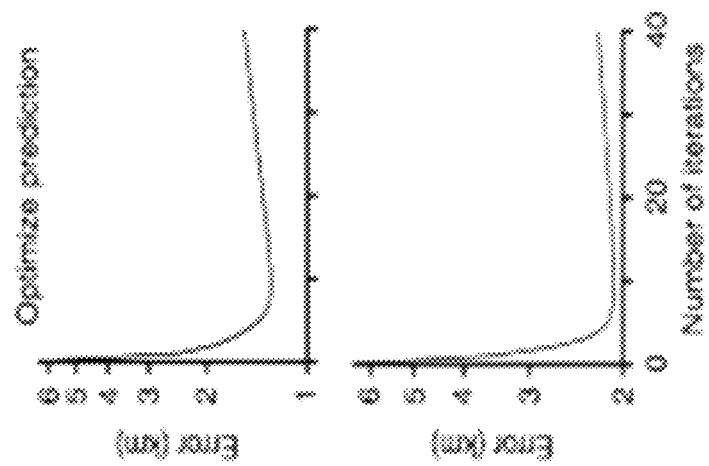
FIG. 6B depicts a window for calculating instantaneous velocity for the position-predictive algorithm in accordance with an illustrative embodiment.
Figure 6A:
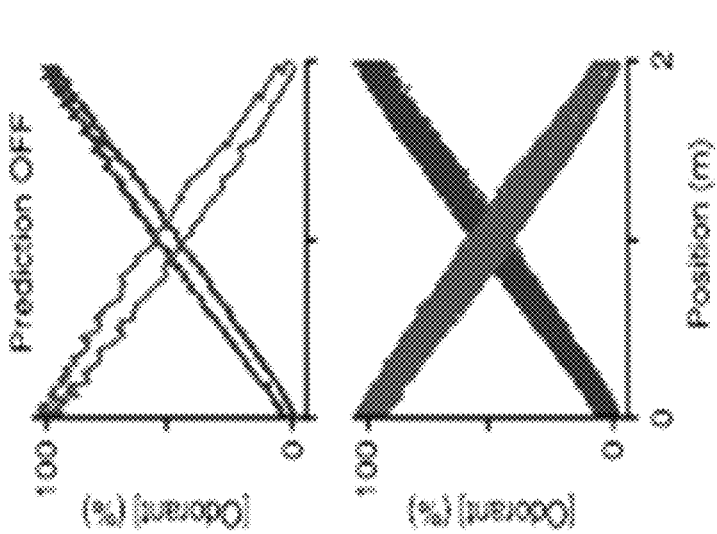
FIG. 6A depicts odorant delivery without use of a position predictive algorithm in accordance with an illustrative embodiment.

FIG. 6A depicts odorant delivery without use of a position predictive algorithm in accordance with an illustrative embodiment. In FIG. 6A, two traversals are depicted, one toward methyl valerate and one toward α-pinene (top), and one for an entire behavioral session (bottom). FIG. 6B depicts a window for calculating instantaneous velocity for the position-predictive algorithm in accordance with an illustrative embodiment. The data in FIG. 6B was optimized offline by minimizing the error between real and predicted position for each odorant. FIG. 6C depicts odorant delivery using the position-predictive algorithm for methyl valerate (top) and α-pinene (bottom) in accordance with an illustrative embodiment. Use of the position-predictive algorithm compensated for the mechanical delay of the system despite variable locomotion velocity, and thus generated precisely controlled odorant concentration gradients.

Figure 6D:
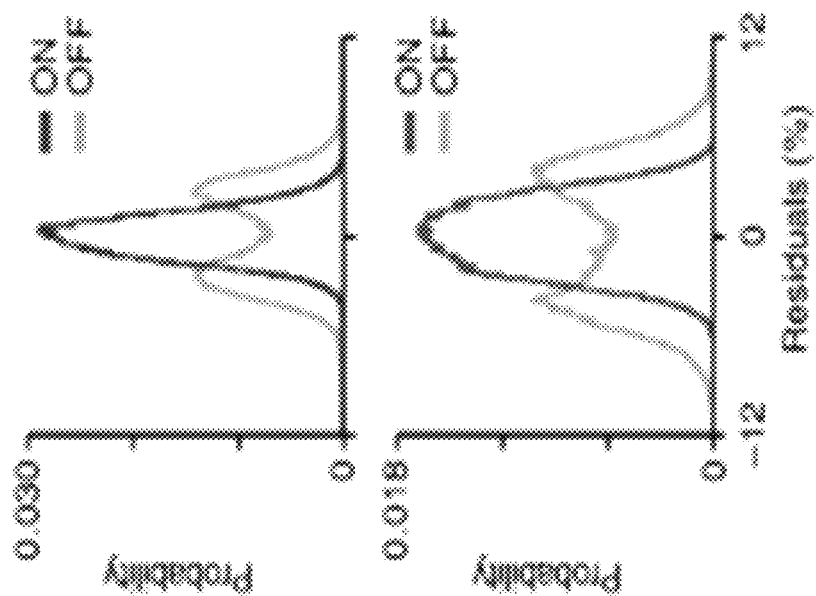
FIG. 6D depicts residuals of the data plotted in FIGS. 6A and 6C to best fit lines in accordance with an illustrative embodiment.
Figure 6C:
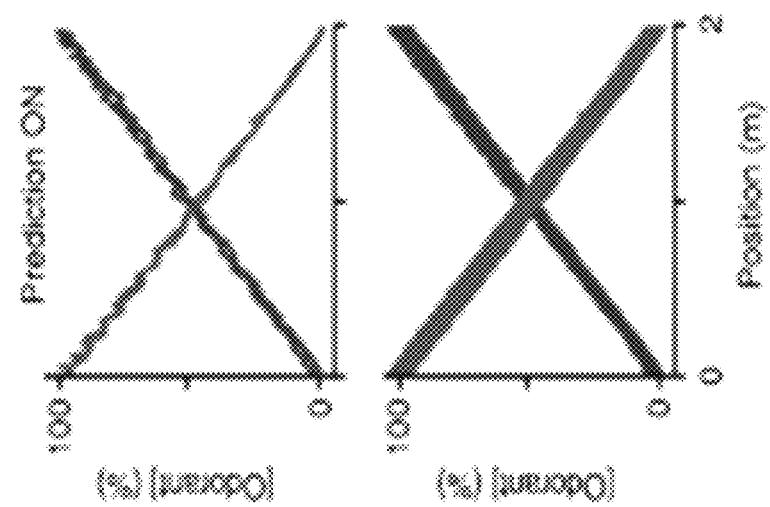
FIG. 6C depicts odorant delivery using the position-predictive algorithm for methyl valerate (top) and $\alpha$-pinene (bottom) in accordance with an illustrative embodiment.

FIG. 6D depicts residuals of the data plotted in FIGS. 6A and 6C to best fit lines in accordance with an illustrative embodiment. It is noted that with the position-predictive algorithm off, a time lag resulted in an odorant distribution that was skewed in the opposite direction of the run, causing a bimodal distribution of residuals (gray), one mode for each run direction, as shown in FIG. 6D. As also shown, this distribution was made unimodal when the position-predictive algorithm was turned on.

The position-predictive algorithm greatly improved system performance. However, the position-predictive algorithm alone was not sufficient for precisely controlling sharp concentration changes characteristic of a noisy odorant distribution. This was due to two additional problems associated with the precise control of odorant distributions. Namely, a variable relationship between the rate of change of MFC flow rate and the resulting odorant concentration change detected at the nose chamber one odorant mechanical delay in the future. Additionally, there was found to be a variable odorant mechanical delay as a function of control drive frequency. These problems, combined with the problems identified above, resulted in a noisy odorant signal that did not represent the spatial frequencies of an idealized noisy distribution when only the position-predictive algorithm was implemented.

To correct for these problems, the frequency components of the ideal (desired) concentration distributions were analyzed, the mean frequency was calculated, and the delays (one for each odor) corresponding to this mean value were chosen. An amplitude correction was then added to the control algorithm to exaggerate the odorant streamflow rates by a magnitude that is a function of the desired concentration change (i.e., the difference between current concentration and desired concentration one odorant mechanical delay in the future). Implementing this combined position-amplitude-predictive algorithm enhanced the frequency components of the desired concentration distribution that the position-only predictive algorithm could not achieve. Using this algorithm, the ideal noisy distributions were replicated with residual errors of 4.3% for methyl valerate and 4.6% for α-pinene and spatial phase lags of 0.00±0.30 cm for methyl valerate and also 0.00±0.30 cm for α-pinene.

Figure 6F:
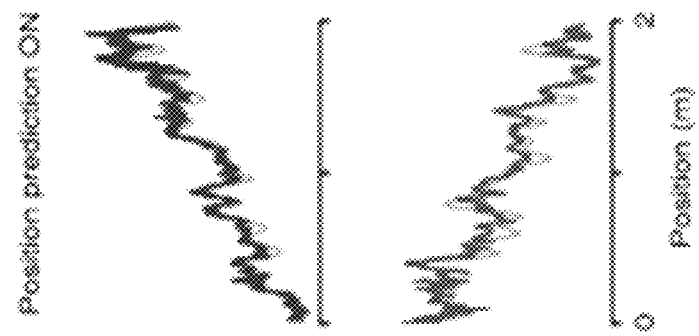
FIG. 6F depicts odorant delivery using only the position-predictive algorithm in accordance with an illustrative embodiment.
Figure 6E:
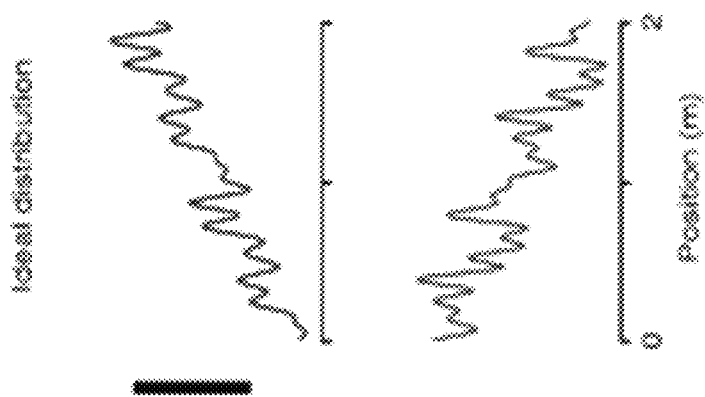
FIG. 6E depicts an ideal noisy odorant distribution for one traversal for methyl valerate (top) and $\alpha$-pinene (bottom) in accordance with an illustrative embodiment.
Figure 6H:
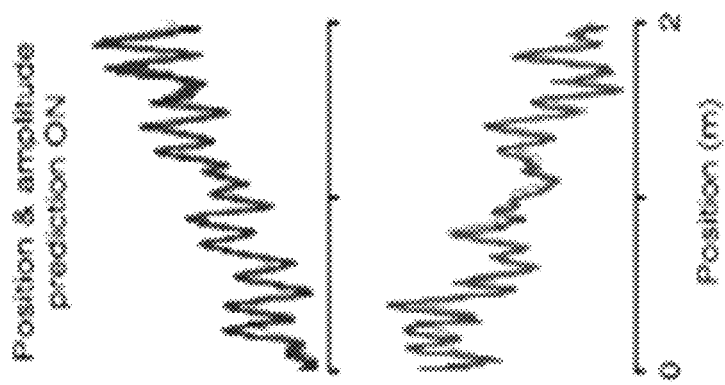
FIG. 6H depicts odorant delivery using a combined position-amplitude-predictive algorithm in accordance with an illustrative embodiment.
Figure 6G:
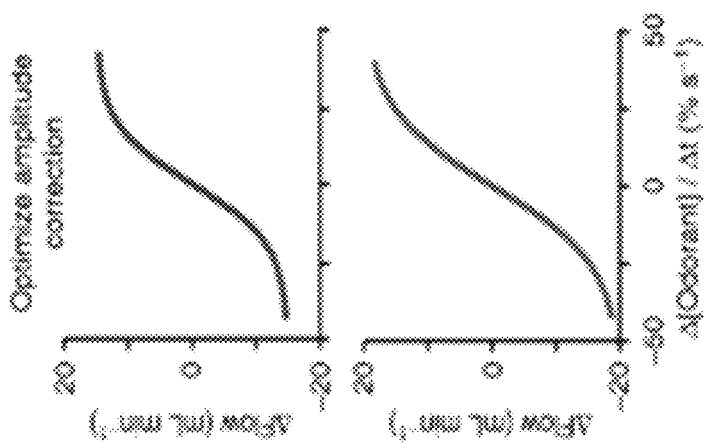
FIG. 6G depicts determination of amplitude correction based on an amount of extra flow needed to achieve a concentration rate of change to generate an ideal odorant distribution in accordance with an illustrative embodiment.
Figure 6J:
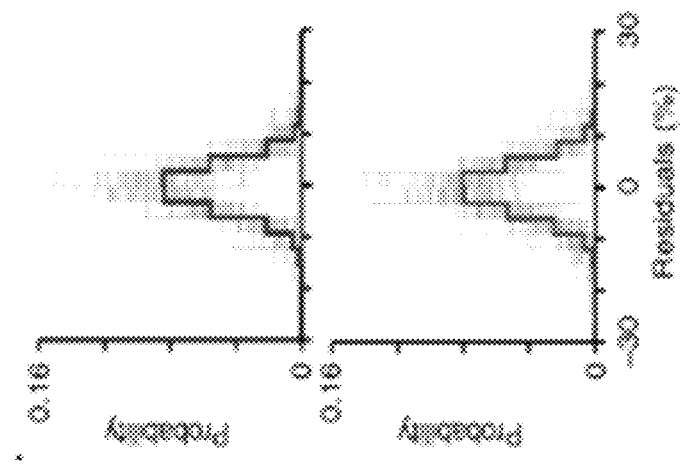
FIG. 6J depicts histograms of the residuals between the real and ideal noisy odorant distributions with the position-amplitude-predictive algorithm on for each traversal (n=205, gray) and for all traversals pooled in accordance with an illustrative embodiment.
Figure 6I:
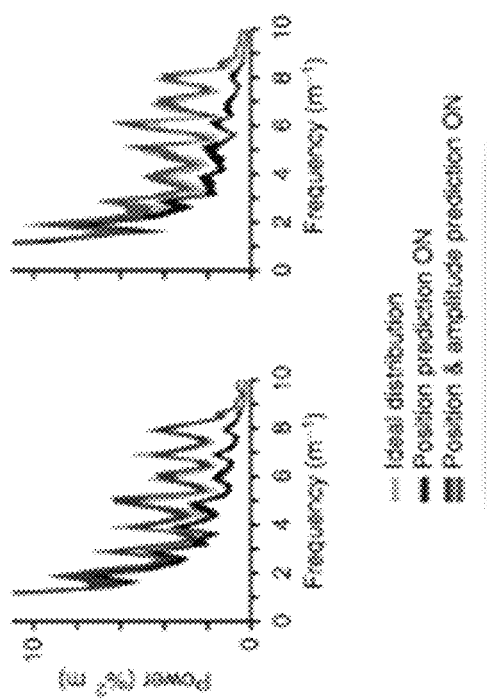
FIG. 6I depicts the power spectra of ideal noisy odorant distributions, real noisy odorant distributions with a position-only predictive algorithm, and real noisy odorant distributions with a position-amplitude predictive algorithm in accordance with an illustrative embodiment.
Figure 6K:
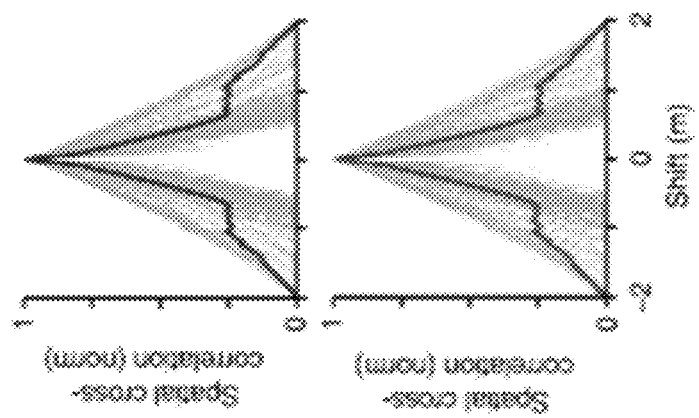
FIG. 6K depicts partial cross-correlation plots between each real and ideal distribution (n=205, gray) and averaged over all distributions in accordance with an illustrative embodiment.

FIG. 6E depicts an ideal noisy odorant distribution for one traversal for methyl valerate (top) and α-pinene (bottom) in accordance with an illustrative embodiment. In FIG. 6E, the scale bar=30%. FIG. 6F depicts odorant delivery using only the position-predictive algorithm in accordance with an illustrative embodiment. FIG. 6G depicts determination of amplitude correction based on an amount of extra flow needed to achieve a concentration rate of change to generate an ideal odorant distribution in accordance with an illustrative embodiment. FIG. 6H depicts odorant delivery using a combined position-amplitude-predictive algorithm in accordance with an illustrative embodiment. FIG. 6I depicts the power spectra of ideal noisy odorant distributions, real noisy odorant distributions with a position-only predictive algorithm, and real noisy odorant distributions with a position-amplitude predictive algorithm in accordance with an illustrative embodiment. In FIG. 6I, n=205 traversals. As shown in FIG. 6I, peaks occurred at the ideal frequencies (integers 1-8 $m^{-1}$) with the position-amplitude predictive algorithm on. FIG. 6J depicts histograms of the residuals between the real and ideal noisy odorant distributions with the position-amplitude-predictive algorithm on for each traversal (n=205, gray) and for all traversals pooled in accordance with an illustrative embodiment. FIG. 6K depicts partial cross-correlation plots between each real and ideal distribution (n=205, gray) and averaged over all distributions in accordance with an illustrative embodiment.

Thus, as shown in FIGS. 6A-6K, incorporation of amplitude to develop a position-amplitude predictive algorithm for users in a virtual reality olfactory system greatly improves the ability to timely delivery the odorants. The position-amplitude predictive algorithm was used to control temporal frequencies up to 4 Hz, which translates to a spatial frequency of up to 8 $m^1$ for a user traveling at a speed of 0.5 m/s. These frequencies are sufficient to simulate odorant bursts measured in a real-world behavioral chamber that occur with a duration of ~0.25 s. Thus, the proposed system can control noisy odorant distributions and turbulent-like plumes, in addition to smooth odorant concentration gradients.

Referring again to FIG. 1, the odorant delivery system is described in more detail below. In alternative embodiments, different values and/or materials may be used. In one embodiment, to deliver odorants with spatial precision to the nose chamber, pressurized air at 20 pounds per square inch (PSI) was run through tubing (e.g., ¼ inch nylon tubing) to a filter (or pre-filter) such as a gas purifier. From the filter, the pressurized air is split and fed into additional tubing (e.g., ¼ inch nylon tubing) to reach the three mass flow controllers (MFCs) in parallel, as shown in FIG. 1. In one embodiment, one or more of the MFCs can be Alicat MC-100SCCM-D MFCs and can have a flow rate 0-0.1 L/min. Outputs of the top and bottom MFCs (in the orientation of FIG. 1) were connected to tubing (e.g., 1/32 inch Teflon tubing) that extends through the caps of the odorant saturation chambers. Specifically, the tubing extends toward a bottom portion of the odorant saturation chambers such that the air flow from the MFCs is forced through liquid (i.e., odorant solution) in the chambers.

In one embodiment, air from the top MFC bubbles into a 12-mL solution of methyl valerate (1:125 methyl valerate: mineral oil) and air from the bottom MFC bubbles into a 12 mL solution of α-pinene (1:37.5 α-pinene:mineral oil). The odorant saturation chambers themselves can be formed from a 40-mL amber glass vial with a rubber membrane cap (or lid) that facilitates the inlet tubing from the MFC and outlet tubing. Other than openings to accommodate inlet tubing and outlet tubing, the cap can seal the odorant saturation chamber from the environment. In alternative embodiments, a larger or smaller odorant saturation chamber may be used, depending on the size of the system and/or the amount of odorant to be used by the system.

The odorant saturation chambers were filled nearly to the top with soda-lime glass beads (diameter 3 mm) to increase air bubble saturation and decrease splashing. Odorant type, concentration, and odorant saturation chamber configuration were optimized empirically to maximize delivery speed while minimizing odorant exhaustion overlong durations. Outlet tubing (e.g., Teflon, 0.002-inch) positioned in the caps of the odorant saturation chambers above the beads/liquid are attached to a passive mixing chamber where the odorant streams meet a stream of blank air delivered by the third MFC. In one embodiment, the third MFC can be an Alicat MC-15SLPM-D/10 M, and can have a flow rate 0-1 L/min. This air-odorant mixture is then led through tubing (e.g., 1/32-inch Teflon tubing) to a custom-made Teflon nose chamber fully covering the nose of the user. In alternative embodiments, different sizes and/or types of tubing may be used in the system.

To eliminate variation in airflow, blank airflow rate was updated dynamically to maintain a constant final flow of 1 L/min. All junctions were secured by threaded Teflon fittings reinforced with Teflon tape, and regularly passed water-immersion leak-checks. All tubing length was minimized, and all tubing diameters were optimized to the minimum possible without compromising MFC operation or causing backflow of odorant solution into the MFCs (through capillary action). To prevent flows in any direction but toward the nose chamber, the odorant stream flow rates were not permitted to fall below 1 mL/min during all odorant delivery sessions, including testing and behavior.

To test the above-described system, relative odorant concentration was measured using a miniature photo-ionization detector (PID) with a flow rate of 950 mL/min placed at the nose chamber. The PID signal, all MFC command and feedback signals, and virtual position and view angle were recorded and synchronized at 1 kHz using a data acquisition card of a computing system. Before each PID measurement, relative odorant concentrations of 0 and 100% were defined as the mean of 5 s of PID signal at flows of 1 and 100 mL/min, respectively. Subsequent measurements were then normalized accordingly. Since the PID cannot simultaneously distinguish two odorants, each PID test was performed separately. To control for any potential variation due to PID placement, the PID was fixed rigidly to the nose chamber for all sequences of measurements. To facilitate odorant clearance, inward- and outward-facing fans were built into a ceiling of the virtual reality chamber used for the testing. At the end of each day of odorant delivery, and between all PID measurements of different odorants, the odorant bottles were removed, submerged tubing was wiped clean, empty bottles were attached, and all MFCs were set to maximum flow rate for 30 min. Fresh odorants solutions in new bottles were mixed daily from stock odorants that were stored in nitrogen gas.

To evaluate the speed of odorant delivery, each odorant MFC was driven by a sinusoid of 0.5 Hz of low or high offset for 150 cycles. Delay between the command and the odorant delivery was calculated as the mean peak-to-peak difference between the command signal and the PID signal. To characterize the speed of odorant delivery as a function of sinusoid frequency, 10 cycles each were applied of all combinations of sinusoids of amplitudes (10, 20, 30, 40, 50, 60, 70, 80, 90, and 99) mL/min and frequencies (0.5, 1, 1.5, 2, 2.5, 3, 3.5, 4, 4.5, and 5) Hz, and the delay for each sinusoid was calculated. Delay was found to be relatively amplitude-invariant at each frequency, and was thus pooled over all amplitudes and plotted as a function of frequency.

To evaluate the stability of odorant delivery, each odor MFC was left at its maximum flow rate of 100 mL/min for ~100 min. A problem for long-duration PID use is drift of the baseline reading. To quantify the PID signal relative to a stable baseline, baseline measurements (odorant streamflow of 1 mL/min) were taken for 1 min every 20 min, and these baseline points were fitted with a second-order polynomial. This polynomial was then subtracted from the non-baseline points. After baseline correction, time constants of depletion were calculated by fitting an exponential to the non-baseline points. It is believed that the methyl valerate was delivered more quickly, but also depleted more quickly because of its higher vapor pressure as compared to α-pinene.

The above-described system was integrated into a visual virtual reality setup, and both visual and olfactory virtual realities were controlled in Matlab using a virtual reality engine with a refresh period of ~5 ms. Flow rates were updated at each iteration of VR using Matlab to send analog voltages to the MFCs via a data acquisition card. To create smooth odorant gradients across a 2 m linear track (FIG. 4), the MFC flow rates F (mL/min) were defined as functions of virtual position x(m):

$$F_1 = 1 + (99/2)x \qquad \text{Equation 1:}$$

$$F_2 = 100 - (99/2)x \qquad \text{Equation 2:}$$

In each of the experimental testing sessions, the carrier stream was set to maintain a constant flow rate of 1000 mL/min, such that:

$$F3 = 1000 - F_1 - F_2 \qquad \text{Equation 3:}$$

Additionally, as discussed above, both position-predictive and position-amplitude predictive algorithms were utilized to improve the timing of odorant delivery based on movement of a user within a VR environment. Development and use of the algorithms is described in more detail below. In alternative embodiments, different values and/or techniques may be used. To apply a position-predictive algorithm to control smooth odorant gradients, the time delays measured as outlined above were selected using 0.5-Hz sinusoids. These delays were 0.148 s for methyl valerate and 0.183 s for α-pinene. These were the times it took from each command signal for each odorant to be received at the nose chamber, and therefore the times Δt in the future that the algorithms needed to predict. Since Δt was different for each odorant, two independent algorithms were implemented to control each odorant stream in parallel. Each algorithm used first-order kinematics at each iteration of VR to predict future position $x_f$ as:

$$x_f = x_0 + v_0 \Delta t \qquad \text{Equation 4:}$$

In Equation 4, $x_0$ is the instantaneous position and $v_0$ is the instantaneous velocity of the user in the VR environment. Since the VR physics engine used in this embodiment did not include an acceleration component, no acceleration term was included in the algorithm. In alternative embodiments, an acceleration term may be incorporated in the algorithms to account for rate of change in the instantaneous velocity. The variable $v_0$ from Equation 4 was calculated as the average of the preceding several Δx/Δt samples as follows:

$$v_0 = \frac{1}{w} \sum_{i=1-w}^{0} \frac{x_i - x_{i-1}}{t_i - t_{i-1}} \qquad \text{Equation 5}$$

In equation 5, w is the smoothing window measured in number of iterations i. As it is not readily apparent how many previous iterations should be averaged to calculate instantaneous velocity, this parameter was optimized offline. To do this, a standard behavior data set was created comprised of 10 min each of good, mediocre, and poor performance (characterized by the reward rate and distance run between rewards) chosen from the behavioral datasets at sampling rate 1 kHz. This testing set was then replayed in VR to simulate behavior in real time, and the positions and timestamps were recorded in order to achieve the same sampling rate as the VR engine (4.9±0.1 ms). Equation 4 was applied offline at each time point to get each predicted position $x_f$. This was done for each value of w from 1 to 40. For each w, error was calculated as the sum of the absolute differences between all predicted positions $x_f$ and their corresponding real future positions $x(t_0 + \Delta t)$ over all n samples as follows:

$$\text{Error} = \Sigma_{i=1}^{n} |x_f - x(t_0 + \Delta t)| \qquad \text{Equation 6:}$$

This error was plotted as a function of w (FIG. 6B), and the optimum window was chosen as the w at which the minimum error occurred. These windows were 9 iterations for methyl valerate and 10 iterations for α-pinene.

To test whether this algorithm reduces the error in the odorant spatial distribution in real time, the PID was placed at the nose chamber and the standard behavior was replayed with the position-predictive algorithm on and off for each odorant. Fresh odorant solutions were used for each replay. To again control for the slow drift intrinsic to the PID, each recording was broken into 5-min blocks and normalized to the best-fit line of PID signal vs position. These normalized blocks were then pooled. The difference between the data and the best-fit line was calculated as the sum of the absolute values of the residuals (FIG. 6D). Performance of the algorithm was visualized by plotting the differences between the data and the best-fit line, i.e., the residuals as shown in FIG. 6D. Improvement bestowed by the algorithm was calculated as the ratio of least absolute deviations with the algorithm off versus on. To remove points during which the user was stationary (i.e., times when the algorithm would be expected to have no effect), only points during which the user was moving faster than 0.1 m/s were included in these plots and calculations.

To simulate a noisy environment, a set of 1000 ideal noisy odorant spatial distributions was created. Each concentration distribution C(x) was defined as a line plus a sum of spatial sinusoids as follows:

$$C(x) = ax + b + \Sigma_{i=1}^{8} A_i \sin(2\pi f_i x + \varphi_i) \quad \text{Equation 7:}$$

In equation 7, the line slope $a = 20\%$ m$^{-1}$, line y-intercept $b = 30\%$ for methyl valerate and $a = -20\%$ m$^{-1}$, $b = 70\%$ for α-pinene. For both odorants, each sine wave amplitude $A_i$ was chosen randomly from (0:6%), each phase offset $\varphi_i$ was chosen randomly from (0:2π) rad, and sine wave spatial frequency $f_i$ was [1, 2, 3, 4, 5, 6, 7, 8] m$^{-1}$.

To simulate a turbulent-like environment, the track used in the experiments was first divided into 24 bins, for a maximum plume rate of 12 plumes m$^{-1}$. Plumes were then randomly assigned to these spatial bins according to the probability distributions:

$$P(x) = 0.05 + 0.20x \quad \text{Equation 8:}$$

$$P(x) = 0.45 - 0.20x \quad \text{Equation 9:}$$

Equation 8 is for methyl valerate and Equation 9 is for α-pinene such that methyl valerate plumes were more likely near $x = 2$ m and α-pinene plumes were more likely near $x = 0$ m. Plume concentration C(x) within a bin was defined as a half-cycle of a rectified spatial sine wave as follows:

$$C(x) = b + |A \sin(2\pi f x)| \quad \text{Equation 10:}$$

In equation 10, $b = 30\%$, plume amplitude A for each plume was chosen randomly from (0:50%), and frequency of the plume waveform $f = 6$ m$^{-1}$ (1 cycle/2 bins). The concentration in bins without plumes was defined as the offset $C(x) = b$. For both the noisy and turbulent like distributions, the corresponding ideal flow distributions were calculated as:

$$F(x) = 1 + \frac{99}{100} C(x) \quad \text{Equation 11}$$

This assumes essentially a 1:1 relationship between flow and concentration at all positions, e.g., 100% odorant always corresponds to the maximum flow of 100 mL/min. A delay Δt was then chosen as being representative of the frequency components of the concentration distribution. In this embodiment, 97 ms and 98 ms were used for methyl valerate and α-pinene, respectively. These values are the delays corresponding to the mean temporal frequency of 2.25 Hz. In alternative embodiments, different values may be used. The position-predictive time window for these delays was then optimized as described above. These windows were 9 iterations for both odorants.

When implemented during VR, a new C(x) distribution was chosen each time the user turned around, i.e., each time its view angle crossed 0 or π radians in any direction, with the bubblegum-ward view angle direction defined as π/2 rad. The index of each chosen distribution and its corresponding timestamp were saved to a file each time a turn-around occurred. When replaying the standard behavior with the position-predictive algorithm on, this method resulted in a somewhat noisy-looking concentration distribution that did not capture the waveforms of the ideal distribution. This implied that the assumption of a 1:1 relationship between flow and concentration was not necessarily correct for fast concentration changes.

To determine the correct relationship between flow and concentration, each odor MFC was driven with a sequence of square pulses of flow amplitude ΔF upward from a baseline flow of 1 mL/min to (5, 10, 15 . . . 100) mL/min, downward from a baseline of 100 mL/min to (95, 91, 87 . . . 1) mL/min, and outward from a baseline of 50 mL/min to (1, 5, 10, 15, . . . 100) mL/min, 10 pulses each, 2 s/pulse, followed by a 2 s baseline. A change in PID signal ΔC was measured at time Δt after the onset of each square pulse. This was done by taking the triggered average of the 10 PID signals and finding the magnitude of the PID signal at time Δt. All (ΔF, ΔC/Δt) pairs were plotted on the same graph for all directions and amplitudes. These plots include both the upstroke and down stroke of each square pulse. The regions of this plot with ΔF between ~−25 and +25 mL/min showed a linear relationship. Thus, the nonlinear regions were discarded and the linear region for each odor was fitted with a line with y-intercept zero of the form:

$$\Delta F = m \frac{\Delta C}{\Delta t} \quad \text{Equation 12}$$

The slopes m of these lines were 0.512 and 0.567 (mL/min)/(% s$^{-1}$) for methyl valerate and α-pinene, respectively. This is the change in flow needed to achieve a 1% concentration change in delay time Δt. These linear fits were suitable for producing turbulent-like distributions, but resulted in overshoots of the ideal concentrations for the noisy distributions. To counteract this overshooting effect, these linear fits were replaced with logistic (sigmoidal) fits with y-intercept zero (FIG. 6G) of the form:

$$\Delta F = \frac{L}{1 + e^{-k(\Delta C/\Delta t)}}, \quad \text{Equation 13}$$

where $L = 15$ and $k = 0.106$ for methyl valerate, and $L = 20$ and $k = 0.080$ for α-pinene.

Flow correction was also implemented during VR, first by replaying the standard behavior for testing and calibration, and subsequently online during user behavior. At each iteration, the predicted position $x_f$ was calculated using Equation 4. The corresponding future ideal concentration $C(x_f)$ from the current ideal noisy distribution was looked up from the previously defined known distribution (Equation 7). The current ideal concentration $C(x_i)$ was subtracted from $C(x_f)$ to get change in concentration ΔC. The corrected flow rate ΔF' needed to achieve the future ideal concentration was then calculated using the ideal flow rate and the flow correction as:

$$\Delta F' = F(x_0) + \Delta F \quad \text{Equation 14:}$$

This resulted in a flow rate that preemptively overshot that of the ideal flow distribution and restored the frequency components of the ideal concentration distribution. To quantify these differences in noise frequencies controlled by the position-predictive vs the position-amplitude-predictive algorithms, all periods of movement of at least 0.5 m were selected, which is far enough to sample at least ¼ of the noisy distribution. For each such period, the real and ideal odorant distributions were binned (averaged) into spatial bins of 1 cm to achieve the same spatial sampling rate, and the spatial power spectral density was then calculated. Over all of these runs through noisy concentration distributions, the average power as a function of spatial frequency was calculated for each algorithm case (FIG. 6I). To eliminate unwanted variability, the behavior and the sequence of noisy distribution choices were set to be identical for each algorithm case.

To quantify the performance of this position-amplitude-predictive algorithm for producing noisy odorant spatial distributions, residuals were calculated between each real and ideal distribution for each traversal and for the entire replayed behavioral session, as shown in FIG. 6J. As the DC offset of the real odorant signal was subject to PID drift and odorant depletion, real and ideal traces on each traversal were aligned by varying the real DC offset until the sum of absolute differences between the real and ideal curves was minimized. Residuals were then calculated. To quantify relative spatial phase between the real and ideal odor curves, the cross-correlation between the real and ideal curve for each traversal was then calculated (FIG. 6K, gray). For presentation, these cross-correlation curves were normalized and averaged, as also shown in FIG. 6K. Spatial phase lag for each traversal was defined as the peak of the cross-correlation.

Figure 7:
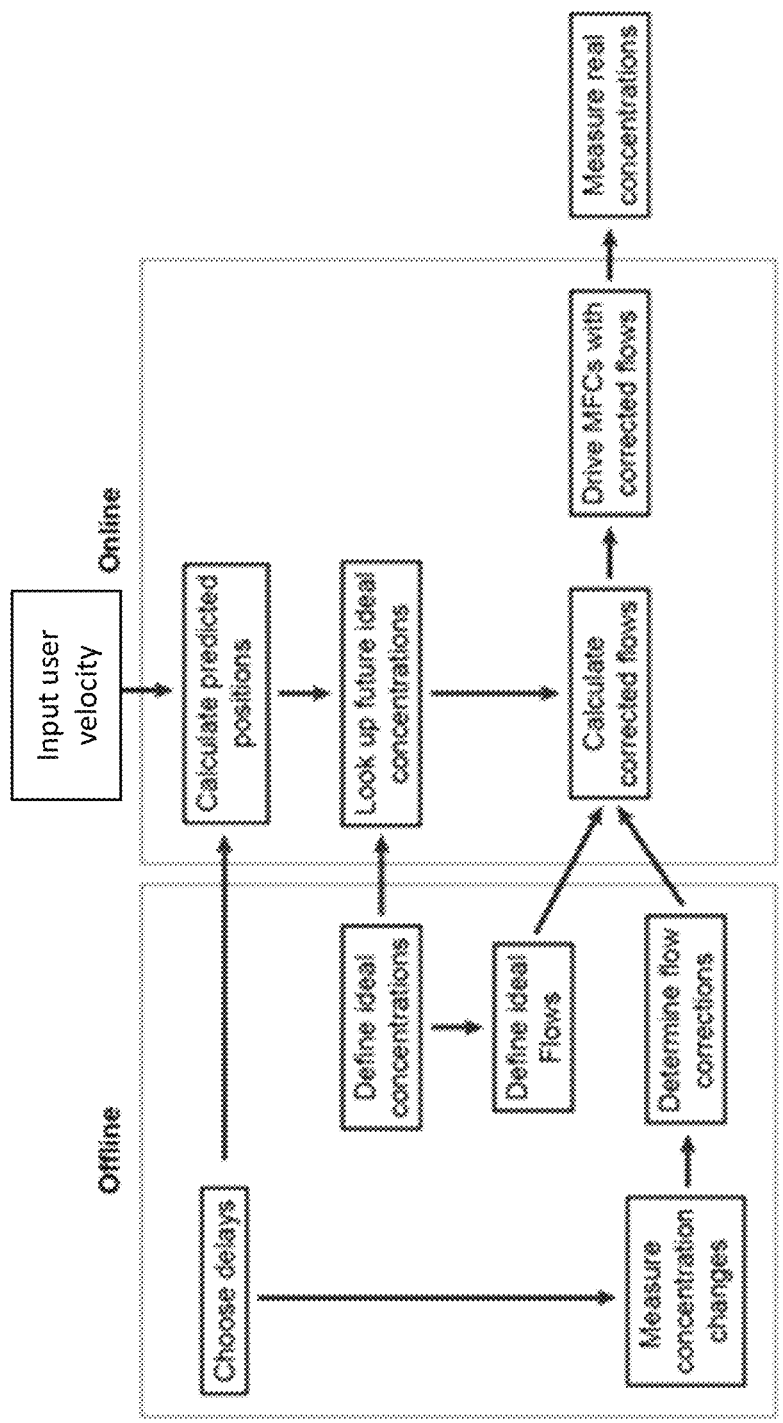
FIG. 7 is a flow diagram depicting operations performed by a position-amplitude-predictive algorithm in accordance with an illustrative embodiment.

FIG. 7 is a flow diagram depicting operations performed by a position-amplitude-predictive algorithm in accordance with an illustrative embodiment. In alternative embodiments, fewer, additional, and/or different operations may be performed. Additionally, the use of a flow diagram is not meant to be limiting with respect to the order of operations performed. As depicted in FIG. 7, the overall process includes online and offline operations. Offline, delays and flow corrections are measured using a PID. Ideal concentrations and flows can be a defined by a system operator. These values can then be fed into the online algorithm that updates at each iteration of VR during usage by a user.

Online, user velocity was used to calculate predicted position at one delay in the future. The ideal concentrations at this predicted position were looked up from the previously defined ideal concentration distributions. For smooth concentration gradients, no further correction was performed. For sharply changing concentrations at fast running speeds, the uncorrected ideal flows were insufficient for achieving the future ideal concentrations, as shown in FIG. 6F. Therefore, the future ideal concentrations were achieved by boosting the ideal flows by the previously determined flow corrections. These corrected flow rates were sent as voltage commands to the MFCs. The resulting odorant concentrations are measured at the nose chamber using the PID as described herein.

Thus, described herein is a virtual reality olfactory apparatus. In one embodiment, the apparatus includes a first odorant saturation chamber and a second odorant saturation chamber. In alternative embodiments in which a different number odorant receptacles are used (e.g., 1, 3, 4, 5, 10, 20, etc.), a different corresponding number of saturation chambers can also be used.

The first odorant saturation chamber can include a first inlet (e.g., hose) that is connected to the first receptacle through a lid of the first receptacle. The first odorant saturation chamber also includes a first outlet (e.g., a hose) that can also extend through the cap. At least a portion of the first odorant saturation chamber can include a first plurality of beads and a first liquid, and the first inlet extends into this portion of the first odorant saturation chamber. The first liquid includes a first odorant concentrate. The second odorant saturation chamber can include a second inlet (e.g., hose) that is connected to the second receptacle through a lid of the second receptacle. The second odorant saturation chamber also includes a second outlet (e.g., a hose) that can also extend through the cap. At least a portion of the second odorant saturation chamber can include a second plurality of beads and a second liquid, and the second inlet extends into this portion of the second odorant saturation chamber. The second liquid includes a second odorant concentrate. As a result of the inlet placement, air coming into the odorant saturation chambers will bubble through the liquid in the chambers to form an odorant.

The apparatus also includes a first mass flow controller configured to generate a first air flow to the first inlet of the first odorant saturation chamber such that the first air flow passes through the portion of the first odorant saturation chamber that includes the first plurality of beads and the first liquid to form a first odorant. The first air flow passes the first odorant through the first outlet of the first odorant saturation chamber. Similarly, a second mass flow controller is configured to generate a second air flow to the second inlet of the second odorant saturation chamber such that the second air flow passes through the portion of the second odorant saturation chamber that includes the second plurality of beads and the second liquid to form a second odorant. The second air flow passes the second odorant through the second outlet of the second odorant saturation chamber. The apparatus can also include a nose chamber connected to the first outlet of the first odorant saturation chamber and the second outlet of the second odorant saturation chamber to receive the first and second odorants.

The apparatus can also include a third mass flow controller in fluid communication with the nose chamber. The third mass flow controller is configured to generate a third air flow to clear or dilute the first odorant and/or second odorant from the nose chamber. The third mass flow controller can further be configured to use the third air flow to maintain a constant flow rate of air through the nose chamber. Alternatively, the flow rate can be dynamic to simulate wind, movement, or other air resistance.

The apparatus can also include a passive mixing chamber connected to the nose chamber. The passive mixing chamber can be configured to receive the first air flow from the first outlet of the first odorant saturation chamber, the second air flow from the second mass flow controller, and the third air flow from the third mass flow controller. In one embodiment, a pre-filter is used to filter air used to generate the first air flow, the second air flow, and the third air flow.

As discussed herein, the apparatus can be used with any virtual reality system known in the art and configured to create a virtual reality environment with olfactory cues for a user. In such an embodiment, the nose chamber can be incorporated into the virtual reality system such that the nose chamber is positioned proximate to a nose of the user of the virtual reality system. The apparatus or system can include computing components such as a processor, memory, transceiver, interface, etc.

Figure 8:
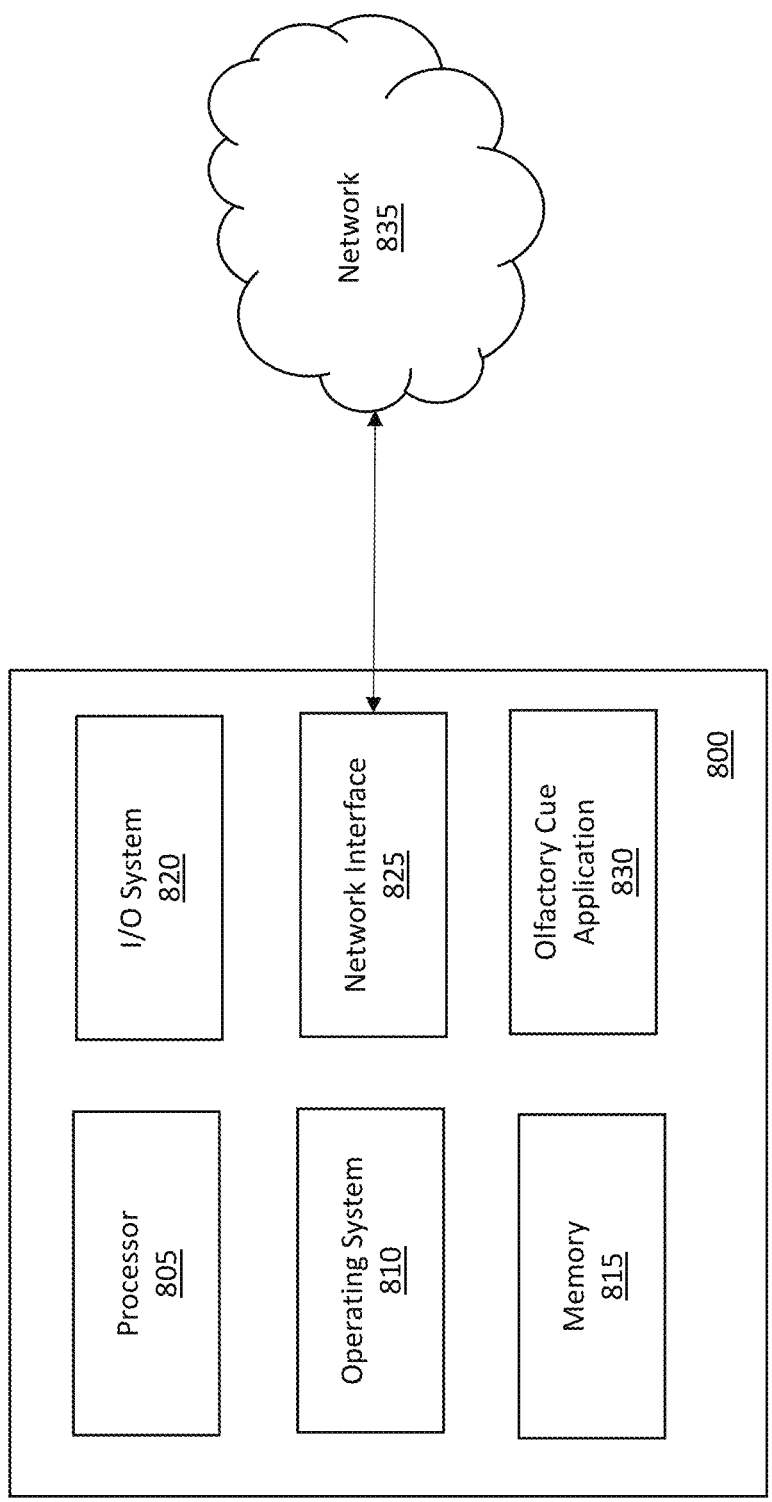
FIG. 8 is a block diagram of a computing device in communication with a network in accordance with an illustrative embodiment.

FIG. 8 is a block diagram of a computing device 800 in communication with a network 835 in accordance with an illustrative embodiment. The computing device 800 can be part of a virtual reality system and/or any other type of computing device that participates in or interacts with the proposed system. The computing device 800 includes a processor 805, an operating system 810, a memory 815, an input/output (I/O) system 820, a network interface 825, and an olfactory cue application 830. In alternative embodiments, the computing device 800 may include fewer, additional, and/or different components. The components of the computing device 800 communicate with one another via one or more buses or any other interconnect system. The computing device 800 can be any type of networked computing device such as a laptop computer, desktop computer, smart phone, tablet, gaming device, workstation, server, a music player device, etc.

The processor 805 can be in electrical communication with and used to control the first, second, and third mass flow controllers described herein. Additionally, in alternative embodiments, additional mass flow controllers may be used to incorporate additional odors into the system. The processor 805 can also be configured to determine a virtual velocity and a virtual bearing of the user in the virtual reality environment using any techniques described herein or known in the art. The processor 805 is also configured to determine a future virtual location of the user within the virtual reality environment based at least in part on the virtual velocity and the virtual bearing, as described herein.

The processor 805 is configured to identify an odorant associated with the future virtual location of the user using the virtual reality system. The processor 805 also identifies the one or more mass flow controllers which are to be activated to form the odorant. The odorant can include the first odorant, the second odorant, a combination of the first odorant and the second odorant, and/or any other combination of odorants in embodiments that include more than two odorant saturation chambers. The processor 805 can also be configured to identify a concentration of the odorant associated with the future virtual location of the user using the virtual reality system, and to control the appropriate MFCs to form the proper concentration. The processor 805 can also be configured to determine a time at which to release the odorant into the nose chamber based at least in part on the virtual velocity of the user. The processor 805 can also determine a duration for which the odorant is to be maintained in the nose chamber. The duration is based at least in part on the virtual velocity of the user. The duration may also be based on other occurrences in the virtual reality environment. The processor 805 can further control the third mass flow controller to remove the odorant from the nose chamber upon expiration of the duration of time. As discussed herein, the processor 805 can identify the odorant in advance of a time at which the user arrives at the future virtual location within the virtual reality environment.

In one embodiment, the processor 805 of the system is configured to issue one or more electronic commands to one or more of the first mass flow controller, the second mass flow controller, and the third mass flow controller to release the odorant and/or airflow into the nose chamber. The processor 805 also determines a time delay between issuance of the one or more electronic commands and delivery of the odorant to the nose chamber. The processor 805 is further configured to correct for the time delay based at least in part on the virtual velocity of the user such that the odorant arrives at the nose chamber at the correct time.

The processor 805 can be any type of computer processor known in the art, and can include a plurality of processors and/or a plurality of processing cores. The processor 805 can include a controller, a microcontroller, an audio processor, a graphics processing unit, a hardware accelerator, a digital signal processor, etc. Additionally, the processor 805 may be implemented as a complex instruction set computer processor, a reduced instruction set computer processor, an x86 instruction set computer processor, etc. The processor 805 is used to run the operating system 810, which can be any type of operating system.

The operating system 810 is stored in the memory 815, which is also used to store programs, user data, network and communications data, peripheral component data, the olfactory cue application 830, and other operating instructions. The memory 815 can be one or more memory systems that include various types of computer memory such as flash memory, random access memory (RAM), dynamic (RAM), static (RAM), a universal serial bus (USB) drive, an optical disk drive, a tape drive, an internal storage device, a non-volatile storage device, a hard disk drive (HDD), a volatile storage device, etc.

The I/O system 820 is the framework which enables users and peripheral devices to interact with the computing device 800. The I/O system 820 can include a mouse, a keyboard, one or more displays, a speaker, a microphone, etc. that allow the user to interact with and control the computing device 800. The I/O system 820 also includes circuitry and a bus structure to interface with peripheral computing devices such as power sources, USB devices, data acquisition cards, peripheral component interconnect express (PCIe) devices, serial advanced technology attachment (SATA) devices, high definition multimedia interface (HDMI) devices, proprietary connection devices, etc.

The network interface 825 includes transceiver circuitry that allows the computing device to transmit and receive data to/from other devices such as remote computing systems, servers, websites, etc. The network interface 825 enables communication through a network 835, which can be one or more communication networks. The network 835 can include a cable network, a fiber network, a cellular network, a wi-fi network, a landline telephone network, a microwave network, a satellite network, etc. The network interface 825 also includes circuitry to allow device-to-device communication such as Bluetooth® communication.

The olfactory cue application 830 can include software in the form of computer-readable instructions which, upon execution by the processor 805, performs any of the various operations described herein such as determining user velocity, determining user position, calculating a future position, determining odorant concentration(s) for future positions, controlling the MFCs to release odorant and airflow, etc. The olfactory cue application 830 can utilize the processor 805 and/or the memory 815 as discussed above. In an alternative implementation, the olfactory cue application 830 can be remote or independent from the computing device 800, but in communication therewith.

As discussed above, in an illustrative embodiment, any of the apparatuses or systems described herein can include and/or be in communication with a computing system that includes, a memory, processor, user interface, transceiver, and any other computing components. Any of the operations described herein may be performed by the computing system. The operations can be stored as computer-readable instructions on a computer-readable medium such as the computer memory. Upon execution by the processor, the computer-readable instructions are executed as described herein.

The word "illustrative" is used herein to mean serving as an example, instance, or illustration. Any aspect or design described herein as "illustrative" is not necessarily to be construed as preferred or advantageous over other aspects or designs. Further, for the purposes of this disclosure and unless otherwise specified, "a" or "an" means "one or more".

The foregoing description of illustrative embodiments of the invention has been presented for purposes of illustration and of description. It is not intended to be exhaustive or to limit the invention to the precise form disclosed, and modifications and variations are possible in light of the above teachings or may be acquired from practice of the invention. The embodiments were chosen and described in order to explain the principles of the invention and as practical applications of the invention to enable one skilled in the art to utilize the invention in various embodiments and with various modifications as suited to the particular use contemplated. It is intended that the scope of the invention be defined by the claims appended hereto and their equivalents.

What is claimed is:

1. A virtual reality olfactory apparatus comprising:
a first odorant saturation chamber, wherein the first odorant saturation chamber includes a cap that has a first inlet and a first outlet, wherein a first portion of the first odorant saturation chamber includes a first plurality of beads and a first liquid and a second portion of the first odorant saturation chamber includes a second plurality of beads and no liquid, wherein the first liquid includes a first odorant concentrate, and wherein the first inlet extends through the cap and into the first portion of the first odorant saturation chamber that includes the first plurality of beads and the first liquid;
a first mass flow controller configured to generate a first air flow to the first inlet of the first odorant saturation chamber such that the first air flow passes through the first portion of the first odorant saturation chamber that includes the first plurality of beads and the first liquid and through the second portion of the first odorant saturation chamber that includes the second plurality of beads and no liquid to form a first odorant, and wherein the first air flow passes the first odorant through the first outlet in the cap of the first odorant saturation chamber; and
a nose chamber connected to the first outlet of the first odorant saturation chamber and configured to receive the first odorant.

2. The apparatus of claim 1, further comprising a second mass flow controller in fluid communication with the nose chamber, wherein the second mass flow controller is configured to generate a second air flow to clear or dilute the first odorant from the nose chamber.

3. The apparatus of claim 2, wherein the second mass flow controller is further configured to use the second air flow to maintain a constant flow rate of air through the nose chamber.

4. The apparatus of claim 2, further comprising a passive mixing chamber connected to the nose chamber, wherein the passive mixing chamber is configured to receive the first air flow from the first outlet of the first odorant saturation chamber and the second air flow from the second mass flow controller.

5. The apparatus of claim 2, further comprising a pre-filter configured to filter air used to generate the first air flow and the second air flow.

6. The apparatus of claim 1, further comprising a virtual reality system configured to create a virtual reality environment for a user, wherein the nose chamber is incorporated into the virtual reality system such that the nose chamber is positioned proximate to a nose of the user of the virtual reality system.

7. The apparatus of claim 6, further comprising:
a second odorant saturation chamber, wherein the second odorant saturation chamber includes a second inlet and a second outlet, wherein at least a portion of the second odorant saturation chamber includes a third plurality of beads and a second liquid, wherein the second liquid includes a second odorant concentrate, and wherein the second inlet extends into the portion of the second odorant saturation chamber that includes the third plurality of beads and the second liquid; and
a second mass flow controller configured to generate a second air flow to the second inlet of the second odorant saturation chamber such that the second air flow passes through the portion of the second odorant saturation chamber that includes the third plurality of beads and the second liquid to form a second odorant, and wherein the second air flow passes the second odorant through the second outlet of the second odorant saturation chamber such that the second odorant is received by the nose chamber.

8. The apparatus of claim 7, further comprising a processor in electrical communication with the first mass flow controller and the second mass flow controller, wherein the processor is configured to determine a virtual velocity and a virtual bearing of the user in the virtual reality environment.

9. The apparatus of claim 8, wherein the processor is configured to determine a future virtual location of the user within the virtual reality environment based at least in part on the virtual velocity and the virtual bearing.

10. The apparatus of claim 9, wherein the processor is configured to identify an odorant associated with the future virtual location of the user, wherein the odorant includes the first odorant, the second odorant, or a combination of the first odorant and the second odorant.

11. The apparatus of claim 10, wherein the processor is configured to identify a concentration of the odorant associated with the future virtual location of the user.

12. The apparatus of claim 10, wherein the processor is configured to determine a time at which to release the odorant into the nose chamber based at least in part on the virtual velocity of the user.

13. The apparatus of claim 10, wherein the processor is configured to:
issue one or more electronic commands to one or more of the first mass flow controller and the second mass flow controller to release the odorant into the nose chamber;
determine a time delay between issuance of the one or more electronic commands and delivery of the odorant to the nose chamber; and
correct for the time delay based at least in part on the virtual velocity of the user.

14. The apparatus of claim 10, wherein the processor identifies the odorant in advance of a time at which the user arrives at the future virtual location within the virtual reality environment.

15. A method for providing olfactory cues in a virtual reality system, the method comprising:
determining, by a processor, a virtual velocity and a virtual bearing of a user in a virtual reality environment;
determining, by the processor, a future virtual location of the user within the virtual reality environment and a time at which the user is to arrive at the future virtual location based at least in part on the virtual velocity and the virtual bearing;
identifying, by the processor, an odorant associated with the future virtual location of the user in advance of the time at which the user is to arrive at the future virtual location within the virtual reality environment; and
controlling, by the processor, one or more mass flow controllers to force air through an inlet positioned in a cap of an odorant saturation chamber, through a first portion of the odorant saturation chamber that includes a first plurality of beads and a liquid that includes the odorant, through a second portion of the odorant saturation chamber that includes a second plurality of beads and no liquid, and through an outlet positioned in the cap of the odorant saturation chamber such that the odorant is released into a nose chamber at the time at which the user is to arrive at the future virtual location.

16. The method of claim 15, wherein identifying the odorant comprises identifying a type of the odorant and a concentration of the odorant.

17. The method of claim 15, further comprising determining, by the processor, a duration of time for which the odorant is to be maintained at the nose chamber.

18. The method of claim 17, further comprising controlling, by the processor, a mass flow controller to remove the odorant from the nose chamber upon expiration of the duration of time.

19. The method of claim 15, wherein the odorant comprises a combination of a first odorant and a second odorant.

* * * * *